United States Patent
Eisinger et al.

(10) Patent No.: US 11,547,412 B2
(45) Date of Patent: Jan. 10, 2023

(54) SURGICAL INSTRUMENTS AND METHODS OF ASSEMBLY

(71) Applicant: Covidien LP, Mansfield, MA (US)

(72) Inventors: Joseph T. Eisinger, Northford, CT (US); Patrick Mozdzierz, Glastonbury, CT (US)

(73) Assignee: Covidien LP, Mansfield, MA (US)

(*) Notice: Subject to any disclaimer, the term of this patent is extended or adjusted under 35 U.S.C. 154(b) by 111 days.

(21) Appl. No.: 16/935,467

(22) Filed: Jul. 22, 2020

(65) Prior Publication Data

US 2022/0022875 A1    Jan. 27, 2022

(51) Int. Cl.
 *A61B 17/072* (2006.01)
 *A61B 17/115* (2006.01)
 *A61B 17/00* (2006.01)

(52) U.S. Cl.
CPC . *A61B 17/1155* (2013.01); *A61B 2017/00473* (2013.01); *A61B 2017/07257* (2013.01); *A61B 2017/07271* (2013.01)

(58) Field of Classification Search
CPC .................................................. A61B 17/1155
USPC ........................................................ 227/175.1
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshln et al. | |
| 4,485,817 A | 12/1984 | Swiggett | |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Thanh K Truong
*Assistant Examiner* — Patrick B Fry
(74) *Attorney, Agent, or Firm* — Carter, DeLuca & Farrell LLP

(57) ABSTRACT

A trocar assembly for use with a circular stapler includes a shaft, a trocar tip, and a band. The trocar tip is configured to mechanically engage a distal portion of the shaft. The trocar tip includes a first portion and a second portion. The first portion of the trocar tip is movable relative to the second portion of the trocar tip prior to assembly of the trocar tip. The band encircles part of the first portion of the trocar tip and part of the second portion of the trocar tip.

20 Claims, 6 Drawing Sheets

(56) References Cited

U.S. PATENT DOCUMENTS

| | | | |
|---|---|---|---|
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Faheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,772,660 A * | 6/1998 | Young | A61B 18/1487 |
| | | | 604/165.01 |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Billner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Dell et al. | |

(56) References Cited

U.S. PATENT DOCUMENTS

| | | |
|---|---|---|
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |

(56) References Cited

U.S. PATENT DOCUMENTS

| | | |
|---|---|---|
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,979,883 B2* | 3/2015 | Smith ............... A61B 17/3496 604/164.01 |
| 2003/0111507 A1 | 6/2003 | Nunez |
| 2004/0073090 A1 | 4/2004 | Butler et al. |
| 2005/0023325 A1* | 2/2005 | Gresham ............ A61B 17/115 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0010842 A1* | 1/2007 | Popov ............... A61B 17/3496 606/185 |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |

(56) References Cited

U.S. PATENT DOCUMENTS

| | | | |
|---|---|---|---|
| 2013/0178885 A1* | 7/2013 | Lee | A61B 17/3423 606/185 |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2016/0051281 A1* | 2/2016 | Hart | A61B 17/3423 600/204 |
| 2016/0143641 A1 | 5/2016 | Sapienza et al. | |
| 2016/0157856 A1 | 6/2016 | Williams et al. | |
| 2016/0174988 A1 | 6/2016 | D'Agostino et al. | |
| 2016/0302792 A1 | 10/2016 | Motai | |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3868310 A1 | 8/2021 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2010045533 A1 | 4/2010 |
| WO | 2016210040 A1 | 12/2016 |
| WO | 2021053445 A1 | 3/2021 |

OTHER PUBLICATIONS

European Examination Report from Appl. No. 14181908.6 dated May 3, 2016.

Extended European Search report dated Dec. 20, 2021 issued in corresponding EP Appln. No 21187113.2.

* cited by examiner

SURGICAL INSTRUMENTS AND METHODS OF ASSEMBLY

BACKGROUND

Technical Field

The present disclosure relates generally to surgical instruments for applying surgical fasteners to body tissue, and to methods of assembling the surgical devices. More particularly, the present disclosure relates to surgical instruments suitable for performing circular anastomosis and/or treatment to internal walls of hollow tissue organs, and methods of assembly.

Background of Related Art

Anastomosis is the surgical joining of separate hollow organ sections. Typically, an anastomosis procedure follows surgery in which a diseased or defective section of hollow tissue is removed, and the end sections are stapled via a linear surgical stapler. Depending on the desired anastomosis procedure, the end sections may be joined by either circular, end-to-end, or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390; 5,588,579; 5,119,983; 5,005,749; 4,646,745; 4,576,167; and 4,473,077, each of which is incorporated herein in its entirety by reference. Typically, these instruments include an elongated shaft having a handle portion at a proximal end to actuate the instrument and a staple holding component disposed at a distal end. After being positioned within tissue, an anvil assembly including an anvil rod with attached anvil head is mounted to the distal end of the instrument adjacent the staple holding component. A trocar of distal end of the instrument may include a band or other indicator which is designed to be covered or occluded by the anvil rod to help ensure proper alignment and engagement between the anvil rod and the trocar.

Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ. Generally, both the actuation of the staple forming mechanism and the advancement of the knife occur at the same time, i.e., simultaneously.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue.

SUMMARY

The present disclosure relates to a trocar assembly for use with a circular stapler. The trocar assembly includes a shaft, a trocar tip, and a band. The trocar tip is configured to mechanically engage a distal portion of the shaft. The trocar tip includes a first portion and a second portion. The first portion is movable relative to the second portion prior to assembly of the trocar tip. The band encircles a part of the first portion of the trocar tip and a part of the second portion of the trocar tip.

In aspects, the first portion of the trocar tip may be movable relative to the second portion between a first position where the first portion and the second portion are free from contact with each other and a second position where the first portion and the second portion are in contact with each other. In aspects, the band may be configured to encircle the part of the first portion of the trocar tip and the part of the second portion of the trocar tip when the first portion and the second portion are in the second position. In further aspects, a distal end of the second portion of the trocar tip may extend farther distally than a proximal end of the first portion of the trocar tip when the first portion and the second portion are in the second position. In additional aspects, a distal most end of the trocar tip may be included on the first portion of the trocar tip.

In aspects, the first portion of the trocar tip may be configured to contact the shaft when the trocar tip is mechanically engaged with the shaft. In further aspects, the second portion of the trocar tip may be configured to contact the shaft when the trocar tip is mechanically engaged with the shaft.

In aspects, the band may be made from blends of polyphenylene oxides or polyphenylene ether resins with polystyrene, a liquid crystal polymer, or polyetheretherketone.

In aspects, the band may be a continuous ring.

The present disclosure also relates to a circular stapler having a handle assembly, an elongated body extending from the handle assembly, and a shell assembly. The shell assembly is disposed adjacent a distal end of the elongated body and includes a cartridge assembly and an anvil assembly. The cartridge assembly includes a trocar assembly. The anvil assembly includes a retention rod configured to selectively engage a portion of the trocar assembly. The trocar assembly includes a shaft, a trocar tip, and a band. The trocar tip is configured to mechanically engage a distal portion of the shaft. The trocar tip has a first portion and second portion. The first portion is movable relative to the second portion between a first position where the first portion and the second portion are free from contact with each other and a second position where the first portion and the second portion are in contact with each other. The band encircles a part of the first portion of the trocar tip and a part of the second portion of the trocar tip when the first portion and the second portion are in the second position. The band is occluded from view when the retention rod of the anvil assembly properly engages the portion of the trocar assembly.

In aspects, a distal end of the second portion of the trocar tip may extend farther distally than a proximal end of the first portion of the trocar tip when the first portion and the second portion are in the second position. In aspects, a distal most end of the trocar tip may be included on the first portion of the trocar tip.

In further aspects, the first portion of the trocar tip may be configured to contact the shaft when the trocar tip is mechanically engaged with the shaft. In aspects, the second portion of the trocar tip may be configured to contact the shaft when the trocar tip is mechanically engaged with the shaft.

In aspects, the band may be made from blends of polyphenylene oxides or polyphenylene ether resins with polystyrene, a liquid crystal polymer, or polyetheretherketone.

In aspects, the band may be a continuous ring.

The present disclosure also relates to a method of assembling a trocar assembly of a surgical instrument. The method includes sliding a band around a part of a first portion of a trocar tip such that the band encircles the part of the first portion, inserting a part of a second portion of the trocar tip between the band and the part of the first portion of the trocar tip, and securing the first portion of the trocar tip to the second portion of the trocar tip.

In aspects, securing the first portion of the trocar tip to the second portion of the trocar tip may occur after sliding the band around the part of the first portion of the trocar tip.

In aspects, securing the first portion of the trocar tip to the second portion of the trocar tip may include welding.

In further aspects, the method may include engaging the trocar tip with a shaft of the trocar assembly such that the first portion of the trocar tip and the second portion of the trocar tip contact the shaft.

DESCRIPTION OF THE DRAWINGS

Various aspects of the present disclosure are illustrated herein with reference to the accompanying drawings, wherein.

DETAILED DESCRIPTION

Aspects of the presently disclosed surgical stapling instrument will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
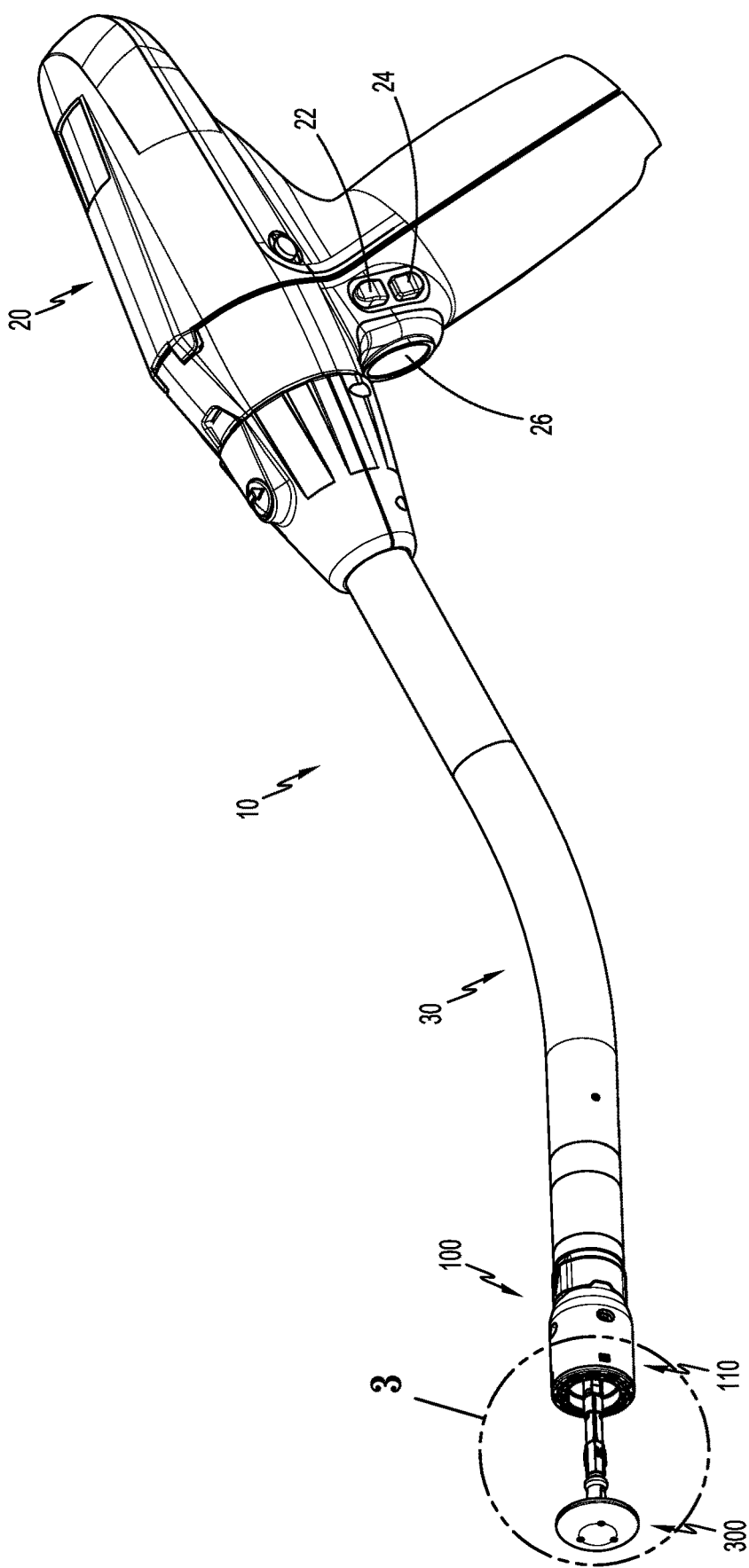
FIG. 1 is a perspective view of a surgical stapling instrument according to aspects of the present disclosure.

FIG. 1 illustrates an aspect of a surgical stapling instrument according to the present disclosure, referenced generally as circular stapler 10. Circular stapler 10 includes a handle assembly 20, an elongated body portion 30 extending distally from handle assembly 20, and a shell assembly 100 mounted adjacent a distal end of elongated body portion 30. The shell assembly 100 includes a cartridge assembly 110 and an anvil assembly 300.

The handle assembly 20 shown in FIG. 1 is a power-operated handle including a first actuator 22, a second actuator 24, and a third actuator 26. While the first actuator 22, the second actuator 24, and the third actuator 26 can be configured to perform at least one function, it is disclosed that the first actuator 22 causes the anvil assembly 300 to move proximally relative to the cartridge assembly 110, the second actuator 24 causes the anvil assembly 300 to move distally relative to the cartridge assembly 110, and the third actuator 26 causes fasteners to be ejected from the cartridge assembly 110 toward the anvil assembly 300.

It is envisioned that the shell assembly 100 may be used with any actuation assembly, powered or manual, and capable of two independent actuation strokes, for example. Commonly owned U.S. Pat. No. 806,973, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members.

It is contemplated that the shell assembly 100 according to the present disclosure can be part of a surgical system. The surgical system can include surgical end effector assemblies (such as shell assembly 100) in various configurations. The elongated body portion 30 of the instrument may itself be a removable and replaceable part of the system. The handle assembly 20 can be manual, powered, or part of a robotic surgical system.

Figure 2:
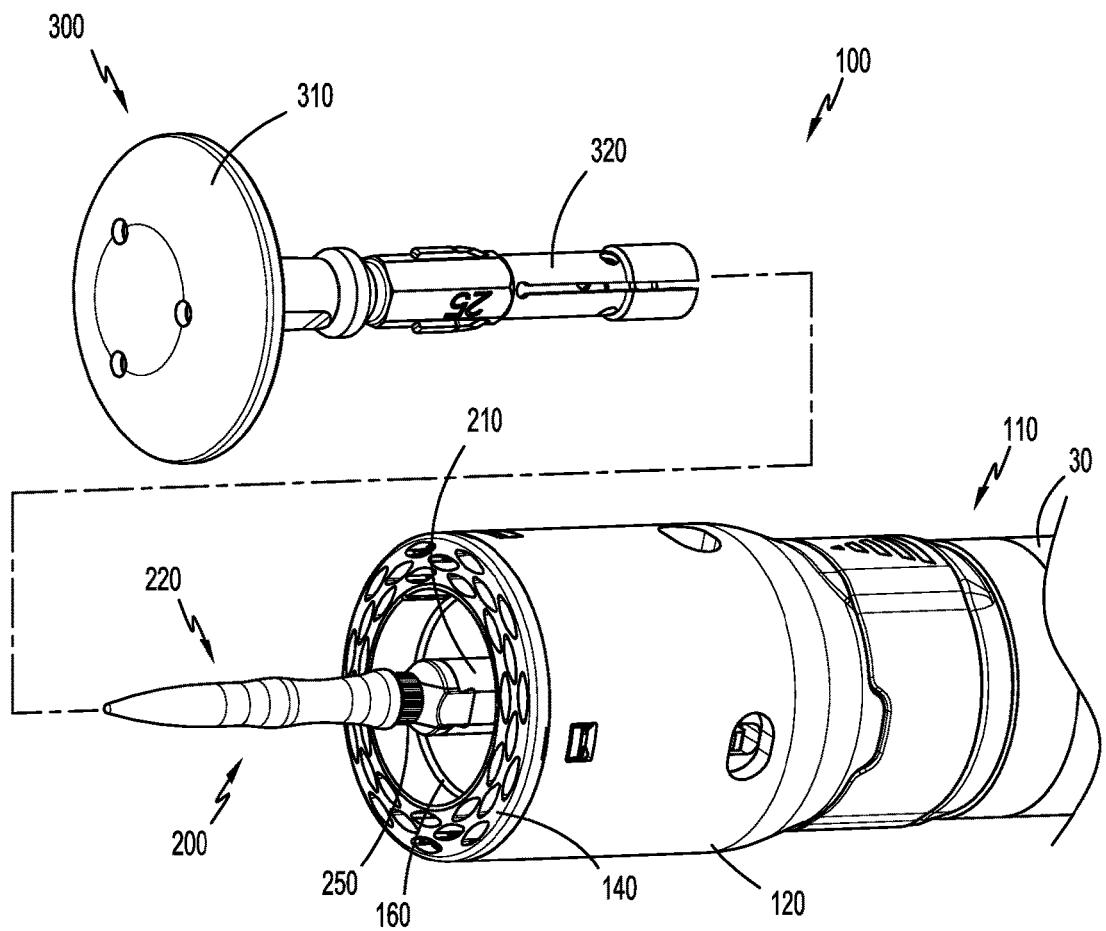
FIG. 2 is an exploded perspective view of a cartridge assembly and an anvil assembly of the surgical stapling instrument of FIG. 1.
Figure 3:
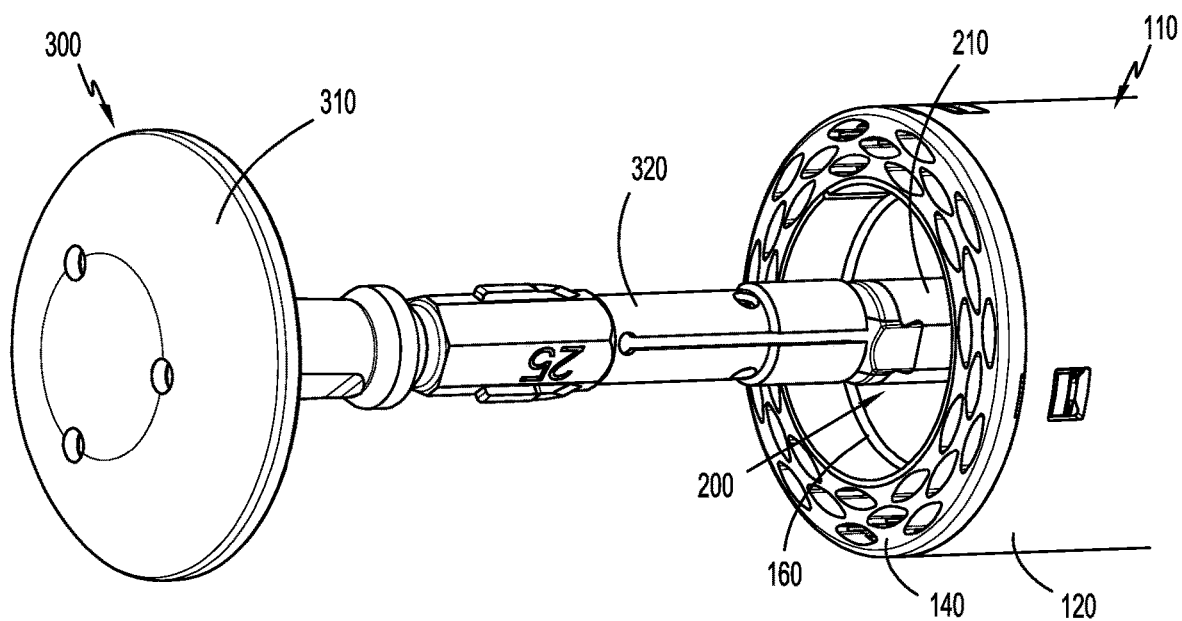
FIG. 3 is an enlarged view of the area of detail indicated in FIG. 1.

With reference to FIGS. 2 and 3, the shell assembly 100 includes the cartridge assembly 110 and the anvil assembly 300. In disclosed aspects, the cartridge assembly 110 is removably secured to and/or within a distal end of the elongated body portion 30 such that the cartridge assembly 110, or a portion thereof, may be replaced and circular stapler 10 may be reused. In other aspects, only a portion of the cartridge assembly 110 is configured to be removed, and subsequently replaced or reloaded. Alternatively, the circular stapler 10 may be configured for a single use, i.e., disposable.

With reference to FIGS. 2 and 3, the cartridge assembly 110 includes a housing 120, a staple cartridge 140, a knife assembly 160, and a trocar assembly 200. The anvil assembly 300 includes an anvil head 310 and a retention rod 320. The anvil head 310 includes a plurality of staple-forming pockets which are configured to deform fasteners ejected from the staple cartridge 140 of the cartridge assembly 110. The retention rod 320 extends proximally from the anvil head 310 and is configured to releasably engage the trocar assembly 200 of the cartridge assembly 110.

With continued reference to FIGS. 2 and 3, the trocar assembly 200 includes a shaft 210, a trocar tip 220 extending distally from the shaft 210 and configured to releasably engage the retention rod 320 of the anvil assembly 300, and a band 250 disposed between the shaft 210 and the trocar tip 220. In use, when the retention rod 320 of the anvil assembly 300 and the trocar tip 220 of the trocar assembly 200 are properly engaged (FIG. 3), a portion of the retention rod 320 covers or occludes the band 250 which provides a visual indication to the user that the cartridge assembly 110 and the anvil assembly 300 are properly engaged.

In other instruments which utilize a similar type of band, the band is added to the trocar assembly 200 either as a coating and/or during a secondary process. Accordingly, the band of such instruments must be made of a limited type of material and may not be as robust as the rest of the trocar assembly, for instance.

Figure 4:
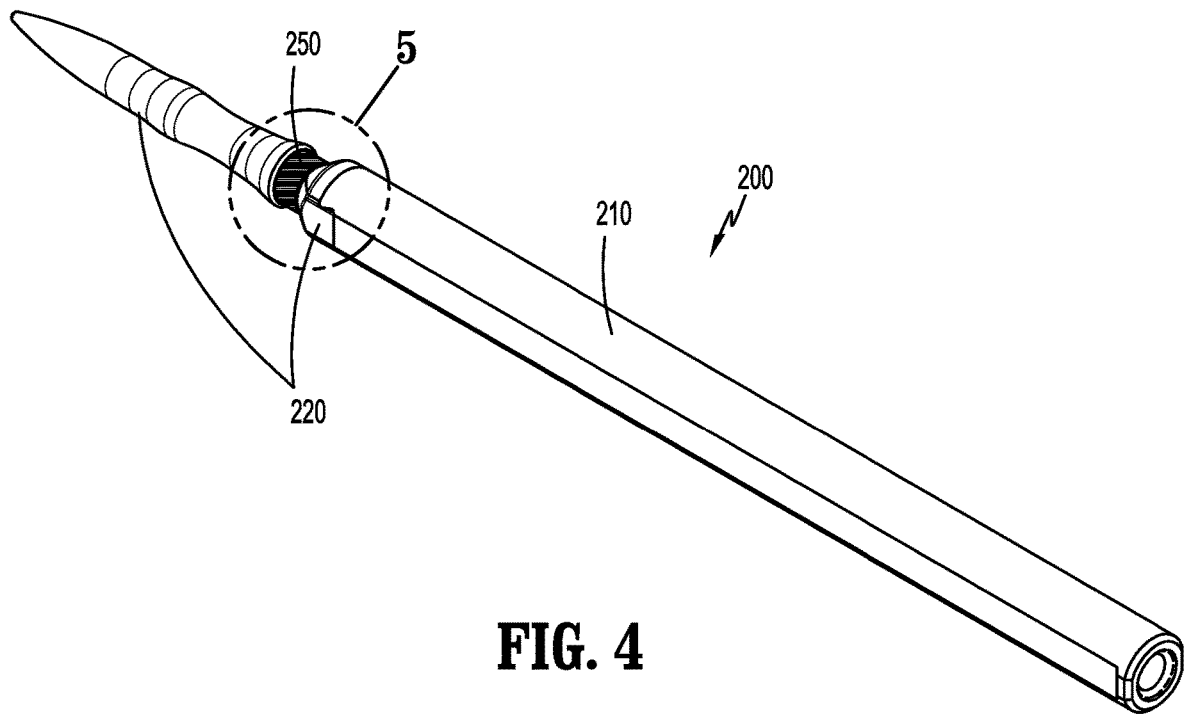
FIG. 4 is a perspective view of a trocar assembly of the surgical stapling instrument of FIGS. 1-3.
Figure 5:
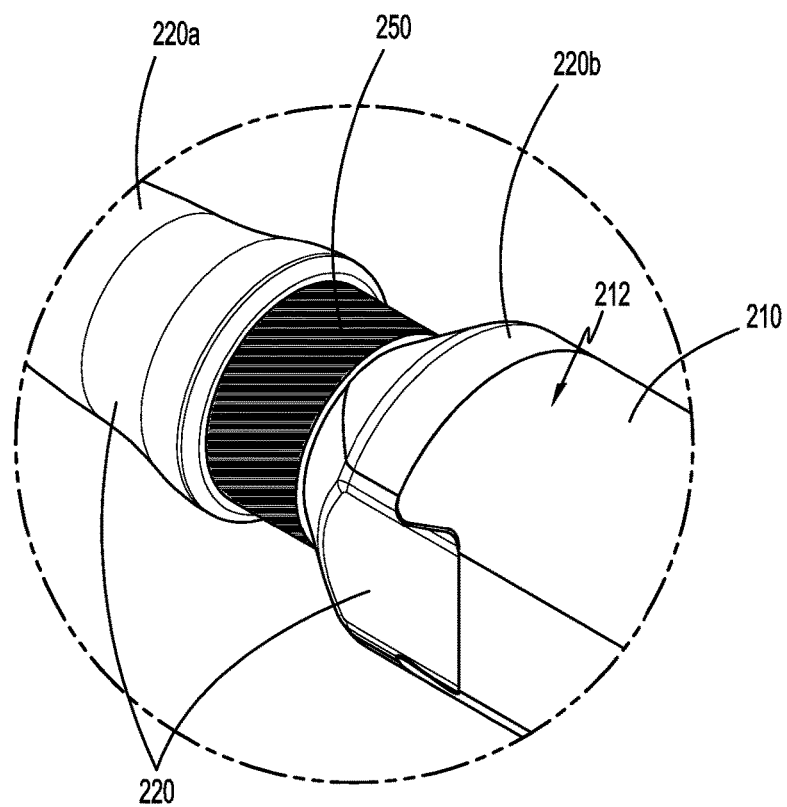
FIG. 5 is an enlarged view of the area of detail indicated in FIG. 4.
Figure 6:
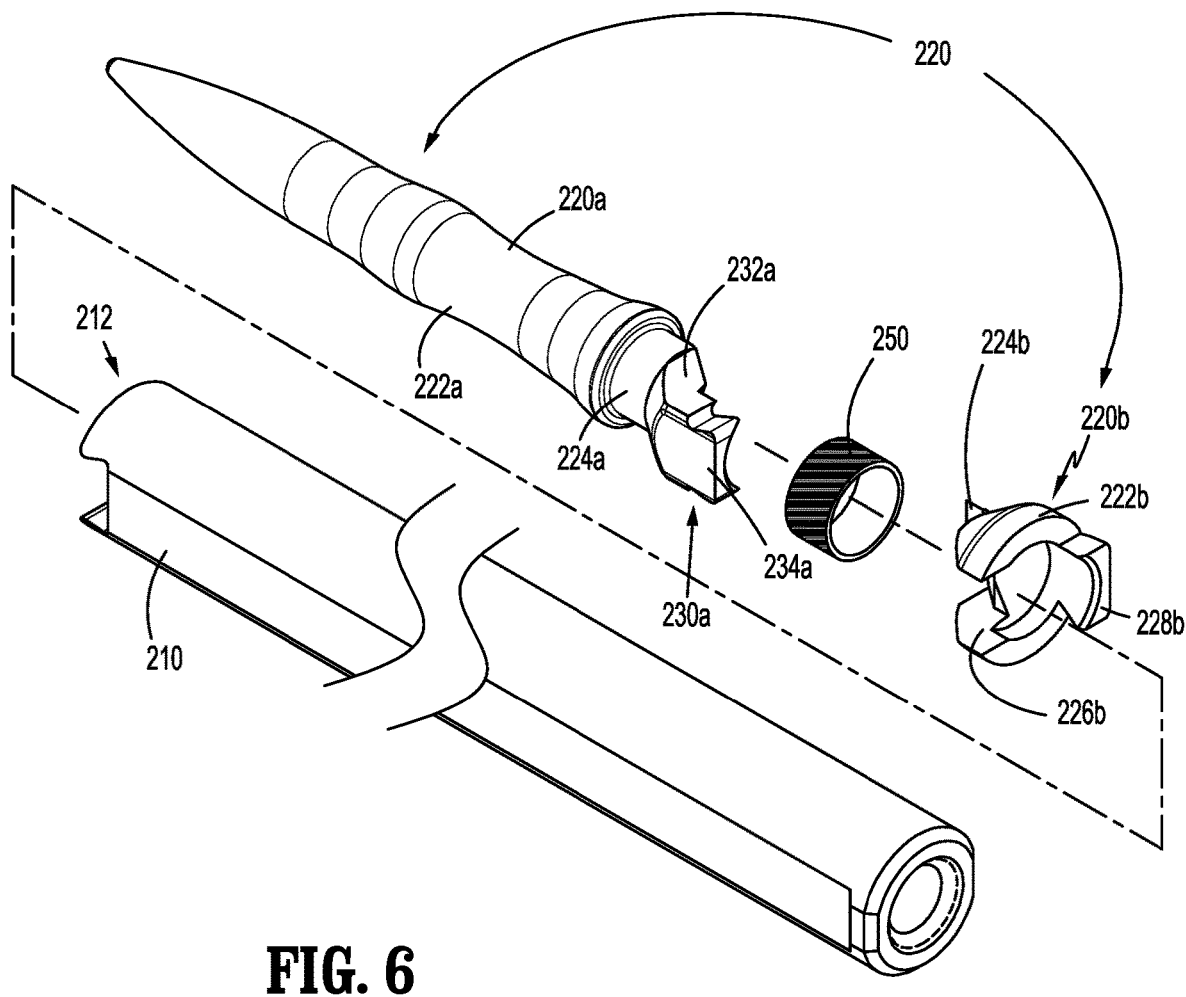
FIG. 6 is a perspective, exploded view of the trocar assembly of FIG. 4.

Referring to FIGS. 4-6, the trocar assembly 200 of the present disclosure includes the band 250 that can be assembled along with the shaft 210 and the trocar tip 220 (as opposed to after assembly of the shaft 210 and the trocar tip 220), thereby allowing the band 250 to be made of materials such as an engineering plastic consisting of amorphous blends of polyphenylene oxides ("PPO") or polyphenylene ether ("PPE") resins with polystyrene (e.g., NORYL®[1]), a liquid crystal polymer (e.g., VECTRA®[2]), or polyetheretherketone ("PEEK"), for instance. Further, since the band 250 is assembled along with the shaft 210 and the trocar tip 220, the band 250 is able to be a unitary ring. In previous instruments utilizing a band, a unitary ring band would be challenging to use at least because the diameter of the band is smaller than the diameter of the distally-adjacent portion of the trocar tip, and is also smaller than the proximally-adjacent portion of the shaft.

[1] Noryl is a registered trademark of SABIC Innovative Plastics IP B.V.
[2] Vectra is a registered trademark of Ticona With particular reference to FIG. 6, to enable the band 250 to be assembled along with the shaft 210 and the trocar tip 220 of the trocar assembly, the trocar tip 220 includes two separate portions: a first portion 220a and a second portion 220b. The first portion 220a of the trocar tip 220 includes an elongated distal portion 222a, a collar 224a, and a proximal portion 230a. The second portion 220b of the trocar tip 220 includes a body portion 222b, and a finger 224b extending distally from the body portion 222b and configured to engage the collar 224a of the first portion 220a of the trocar tip 220.

More specifically, the proximal portion 230a of the first portion 220a of the trocar tip 220 includes a first ramp 232a, a second ramp (opposite the first ramp 232a and hidden from view in FIG. 6), and a lateral extension 234a. The body 222b of second portion 220b of the trocar tip 220 includes a first ramp (hidden from view in FIG. 6), a second ramp 226b, and a lateral extension 228b. The first ramp 232a of the first portion 220a is configured to engage the first ramp of the second portion 220b. The second ramp of the first portion 220a is configured to engage the second ramp 226b of the second portion 220b. Both the lateral extension 234a of the first portion 220a and the lateral extension 228b of the second portion 220b are configured to engage a distal end 212 of the shaft 210.

Figure 7:
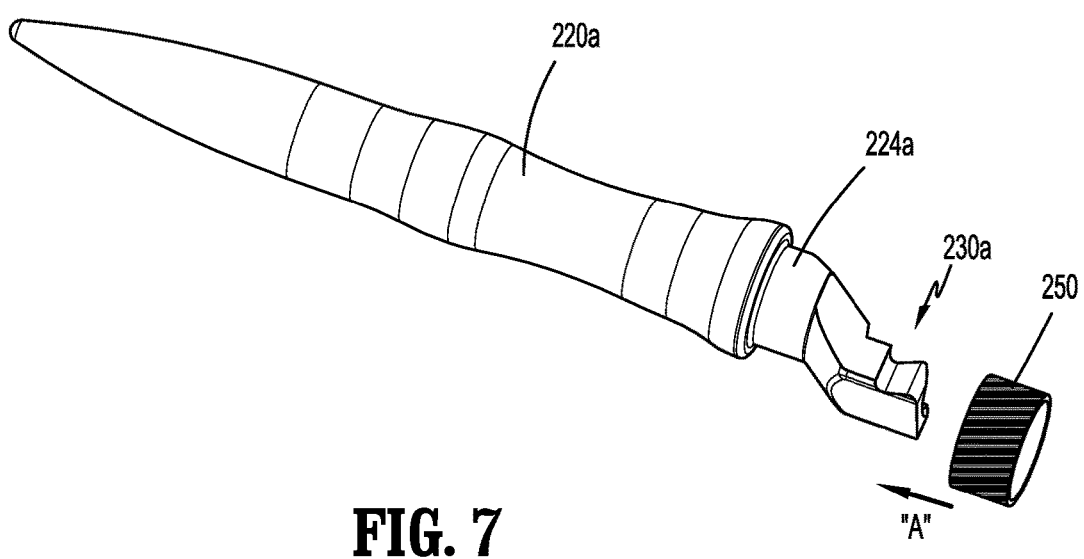
FIGS. 7-10 are perspective views of the trocar assembly of FIG. 4 shown during different stages of assembly.
Figure 8:
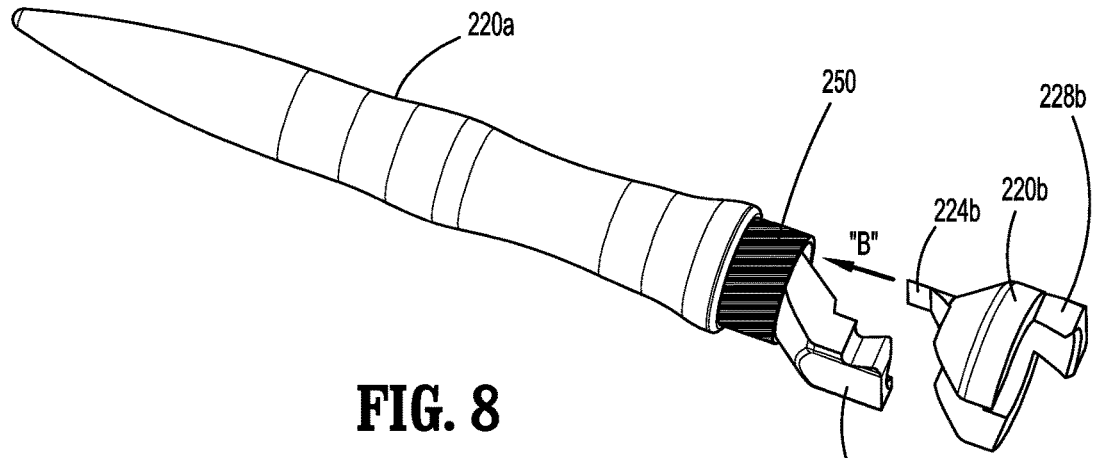
Figure 9:
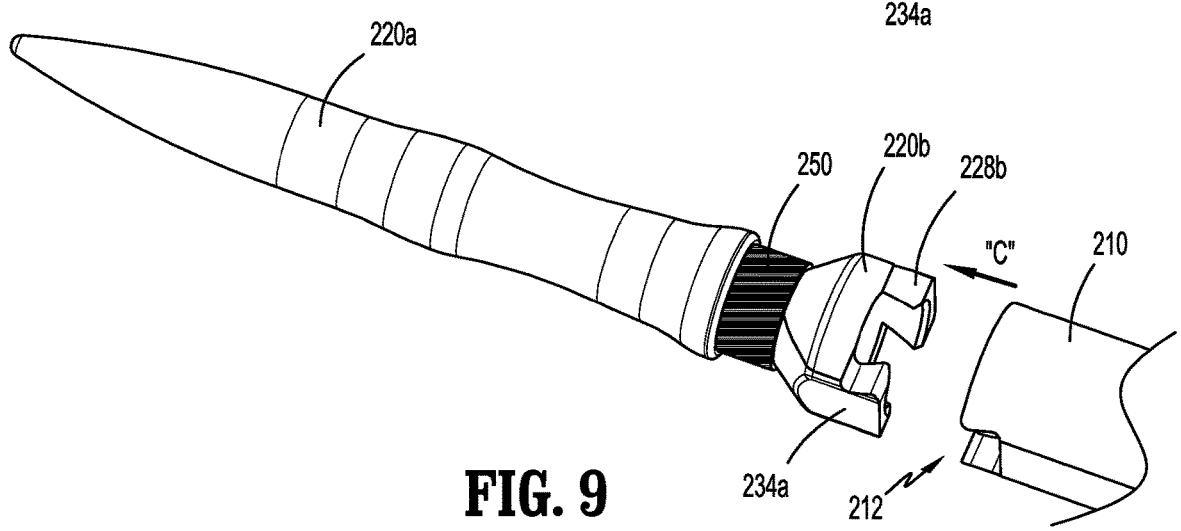

Various steps of assembly of the trocar assembly 200 are shown in FIGS. 7-10. Initially, as shown in FIG. 7, the band 250 is moved distally in the general direction of arrow "A" relative to the first portion 220a of the trocar tip 220. The band 250 is moved distally past the proximal portion 230a of the first portion 220a of the trocar tip 220, and is positioned such that the band 250 radially surrounds the collar 224a of the first portion 220a, as shown in FIG. 8. Next, with continued reference to FIG. 8, the second portion 220b of the trocar tip 220 is moved distally in the general direction of arrow "B" relative to the first portion 220a of the trocar tip 220 and relative to the band 250. During this distal movement of the second portion 220b, the finger 224b of the second portion 220b is inserted between the band 250 and the collar 224a (occluded from view in FIG. 8) of the first portion 220a of the trocar tip 220. As shown in FIG. 9, when the first portion 220a and the second portion 220b of the trocar tip 220 are engaged, the band 250 encircles the collar 224a of the first portion 220a and the distal finger 224b of the second portion 220b. The first portion 220a and the second portion 220b of the trocar tip 220 may then be welded together or otherwise secured.

Figure 10:
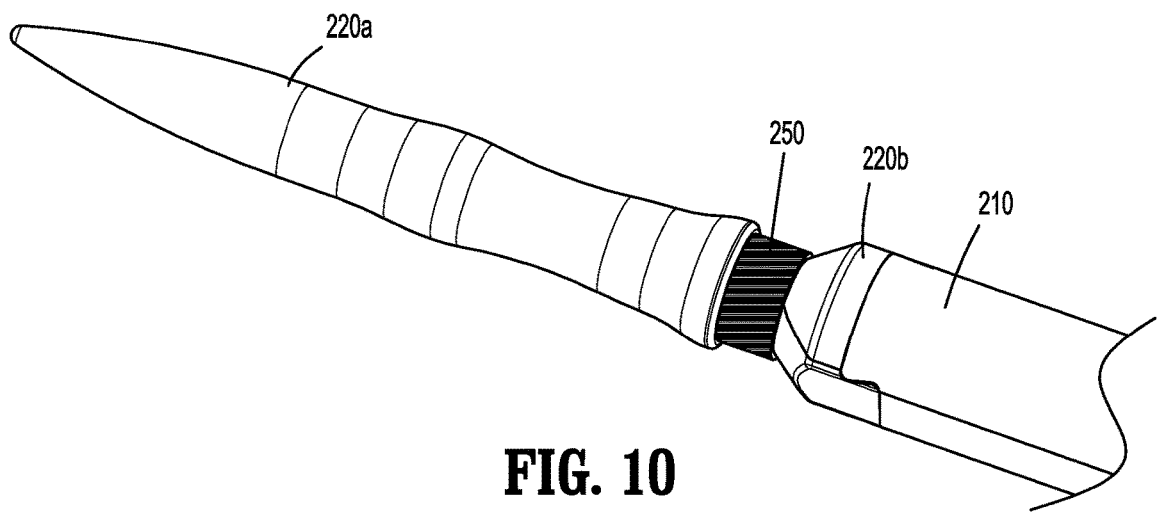

As shown in FIG. 9, the shaft 210 of the trocar assembly 200 is then moved distally in the general direction of arrow "C" relative to the trocar tip 220 such that the distal end 212 of the shaft 210 engages (e.g., via snap-fit connection) both the first portion 220a of the trocar tip 220 (at the lateral extension 234a) and the second portion 220b of the trocar tip 220 (at the lateral extension 228b). FIG. 10 illustrates the shaft 210 of the trocar assembly 200 engaged with the trocar tip 220 of the trocar assembly 200.

FIGS. 11-14 illustrate a trocar assembly 2000 (or portions thereof) in accordance with a second aspect of the present disclosure. Trocar assembly 2000 is configured for use with the shell assembly 100 of the circular stapler 10 in place of the trocar assembly 200 of FIGS. 6-10, for instance. For clarity, some common features between the trocar assembly 2000 and the trocar assembly 200 will not be discussed in detail.

Figure 11:
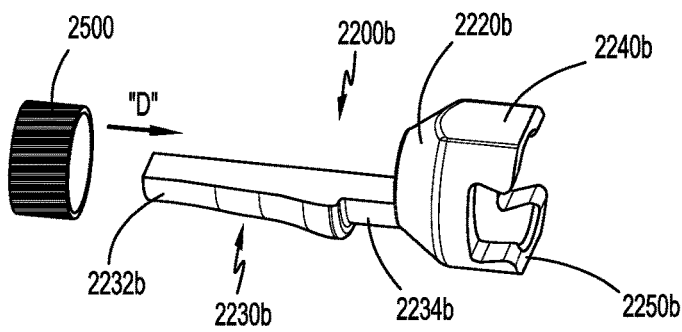
FIGS. 11-14 are perspective views of a trocar assembly according to a different aspect of the present disclosure shown during different stages of assembly.
Figure 12:
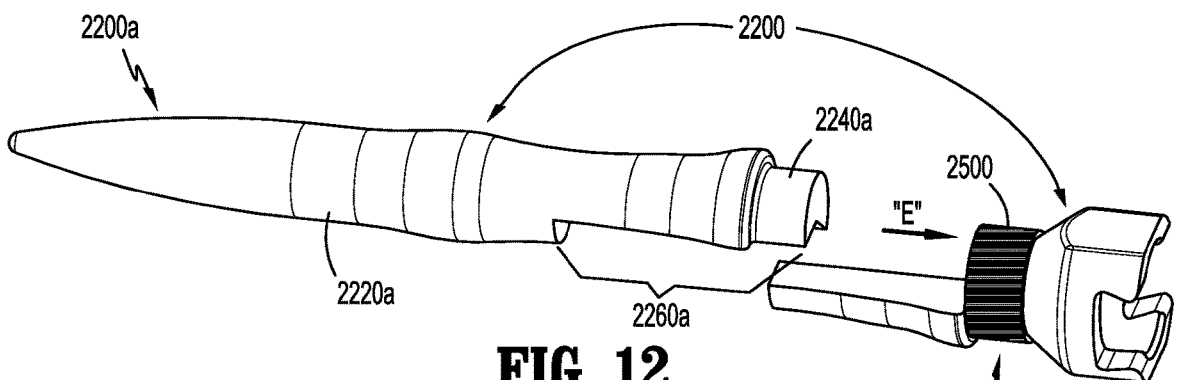

The trocar assembly 2000 includes a shaft 2100, a trocar tip 2200, and a band 2500. With particular reference to FIGS. 11 and 12, to enable the band 2500 to be assembled along with the shaft 2100 and the trocar tip 2200 (as opposed to after the shaft and trocar tip are assembly), the trocar tip 2200 includes two separate portions: a first portion 2200a and a second portion 2200b. As shown in FIG. 12, the first portion 2200a of the trocar tip 2200 includes an elongated distal portion 2220a, a collar 2240a, and a notch 2260a. The notch 2260a extends longitudinally through the collar 2240a and through part of the elongated distal portion 2220a.

As shown in FIGS. 11 and 12, the second portion 2200b of the trocar tip 2200 includes a body portion 2220b, a finger 2230b extending distally from the body portion 2220b, a first lateral extension 2240b extending proximally from the body portion 2220b, and a second lateral extension 2250b extending proximally from the body portion 2220b. The finger 2230b includes an elongated distal portion 2232b and a collar portion 2234b.

Various steps of assembly of the trocar assembly 2000 are shown in FIGS. 11-14. Initially, as shown in FIG. 11, the band 2500 is moved proximally in the general direction of arrow "D" relative to the second portion 2200b of the trocar tip 2200. The band 2500 is moved proximally past the elongated distal portion 2232b of the finger 2230b of the second portion 2200b of the trocar tip 2200, and is positioned such that the band 2500 radially surrounds the collar portion 2234b of the finger 2230b, as shown in FIG. 12. Next, with continued reference to FIG. 12, the first portion 2200a of the trocar tip 2200 is moved proximally in the general direction of arrow "E" relative to the second portion 2200b of the trocar tip 2200 and relative to the band 2500. During this proximal movement of the first portion 2200a, the collar 2240a of the first portion 2200a is inserted between the band 2500 and the collar portion 2234b of the second portion 2200b of the trocar tip 2200. Additionally, during this proximal movement of the first portion 2200a, the finger 2230b of the second portion 2200b engages with the notch 2260a of the first portion 2200a. The first portion 2200a and the second portion 2200b of the trocar tip 2200 may then be welded together or otherwise secured.

Figure 13:
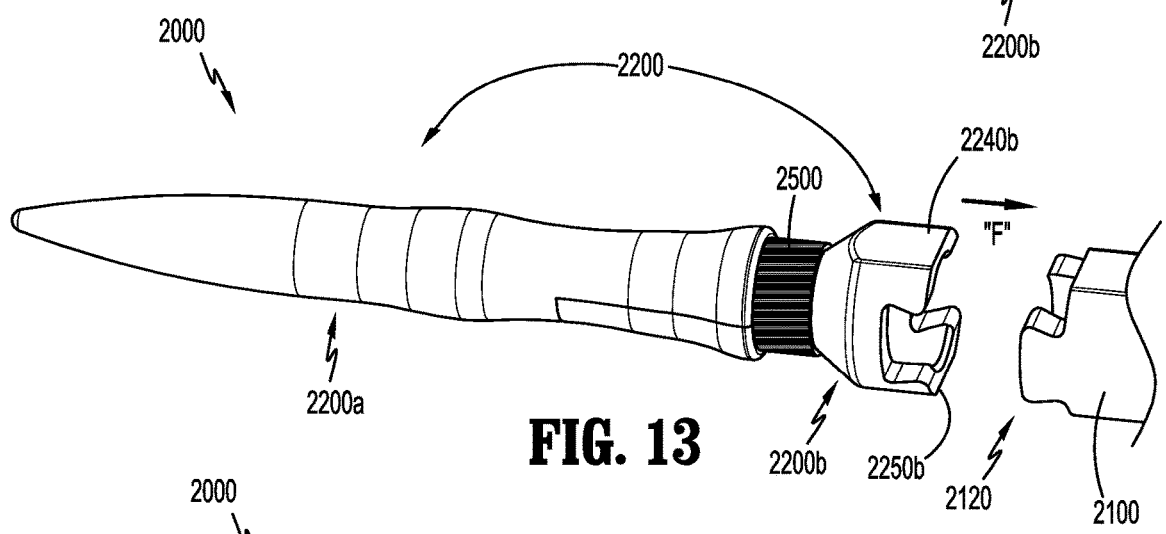

As shown in FIG. 13, when the first portion 2200a and the second portion 2200b of the trocar tip 2200 are engaged, the band 2500 encircles the collar 2240a of the first portion 2200a and the collar portion 2234b of the second portion 2200b.

Figure 14:
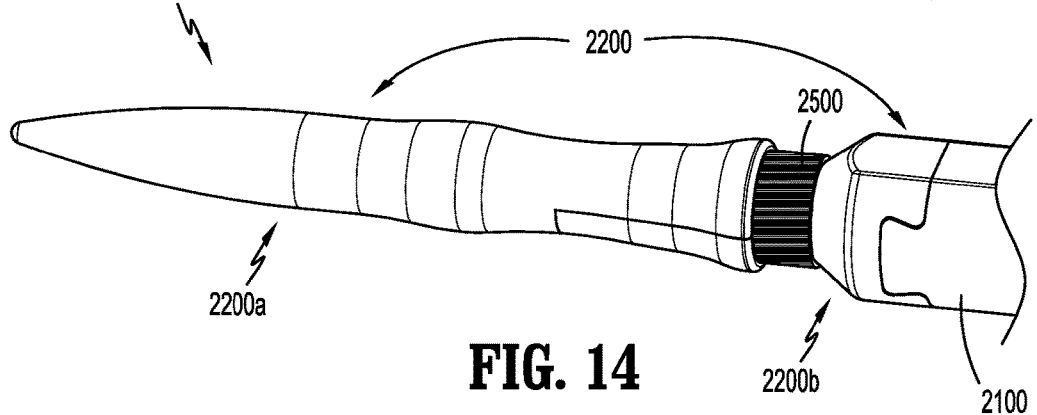

With continued reference to FIG. 13, the trocar assembly 2000 is then moved proximally in the general direction of arrow "F" relative to the shaft 2100 such that a distal end 2120 of the shaft 2100 engages (e.g., via snap-fit connection) the first lateral extension 2240b and the second lateral extension 2250b of the second portion 2200b of the trocar tip 2200; the shaft 2100 does not contact the first portion 2200a of the trocar tip 2200. FIG. 14 illustrates the shaft 2100 of the trocar assembly 2000 engaged with the trocar tip 2200 of the trocar assembly 2000.

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. A trocar assembly for use with a circular stapler, the trocar assembly comprising:
    a shaft;
    a trocar tip configured to mechanically engage a distal portion of the shaft, the trocar tip including a first portion and second portion, the first portion is movable relative to the second portion prior to assembly of the trocar tip, each of the first portion of the trocar tip and the second portion of the trocar tip is configured to contact the shaft when the trocar tip is mechanically engaged with the shaft; and
    a band encircling a part of the first portion of the trocar tip and a part of the second portion of the trocar tip.

2. The trocar assembly according to claim 1, wherein the first portion of the trocar tip is movable relative to the second portion between a first position where the first portion and the second portion are free from contact with each other and a second position where the first portion and the second portion are in contact with each other.

3. The trocar assembly according to claim 2, wherein the band is configured to encircle the part of the first portion of the trocar tip and the part of the second portion of the trocar tip when the first portion and the second portion are in the second position.

4. The trocar assembly according to claim 2, wherein a distal end of the second portion of the trocar tip extends farther distally than a proximal end of the first portion of the trocar tip when the first portion and the second portion are in the second position.

5. The trocar assembly according to claim 4, wherein a distal most end of the trocar tip is included on the first portion of the trocar tip.

6. The trocar assembly according to claim 1, wherein the band is made from blends of polyphenylene oxides or polyphenylene ether resins with polystyrene, a liquid crystal polymer, or polyetheretherketone.

7. The trocar assembly according to claim 1, wherein the band is a continuous ring.

8. A circular stapler comprising:
    a handle assembly;
    an elongated body extending from the handle assembly; and
    a shell assembly disposed adjacent a distal end of the elongated body and including a cartridge assembly and an anvil assembly, the cartridge assembly including a trocar assembly, and the anvil assembly including a retention rod configured to selectively engage a portion of the trocar assembly, the trocar assembly including:
    a shaft;
    a trocar tip configured to mechanically engage a distal portion of the shaft, the trocar tip having a first portion and second portion, the first portion is movable relative to the second portion between a first position where the first portion and the second portion are free from contact with each other and a second position where the first portion and the second portion are in contact with each other; and
    a band encircling a first part of the first portion of the trocar tip and a first part of the second portion of the trocar tip when the first portion and the second portion are in the second position, wherein a second part of the first portion of the trocar tip extends proximally of the band, a second part of the second portion of the trocar tip extends proximally of the band, and the band is occluded from view when the retention rod of the anvil assembly properly engages the portion of the trocar assembly.

9. The circular stapler according to claim 8, wherein a distal end of the second portion of the trocar tip extends farther distally than a proximal end of the first portion of the trocar tip when the first portion and the second portion are in the second position.

10. The circular stapler according to claim 9, wherein a distal most end of the trocar tip is included on the first portion of the trocar tip.

11. The circular stapler according to claim 8, wherein the first portion of the trocar tip is configured to contact the shaft when the trocar tip is mechanically engaged with the shaft.

12. The circular stapler according to claim 11, wherein the second portion of the trocar tip is configured to contact the shaft when the trocar tip is mechanically engaged with the shaft.

13. The circular stapler according to claim 8, wherein the band is made from blends of polyphenylene oxides or polyphenylene ether resins with polystyrene, a liquid crystal polymer, or polyetheretherketone.

14. The circular stapler according to claim 8, wherein the band is a continuous ring.

15. A trocar assembly for use with a circular stapler, the trocar assembly comprising:
    a shaft;
    a trocar tip configured to mechanically engage a distal portion of the shaft, the trocar tip including a first portion and second portion, the first portion is movable relative to the second portion prior to assembly of the trocar tip; and
    a band encircling a part of the first portion of the trocar tip and a part of the second portion of the trocar tip, wherein a diameter of the band is smaller than a diameter of a portion of the trocar tip that is disposed proximally-adjacent the band when the trocar tip is mechanically engaged with the shaft.

16. The trocar assembly according to claim 15, wherein the diameter of the band is smaller than a diameter of a portion of the trocar tip that is disposed distally-adjacent the band when the trocar tip is mechanically engaged with the shaft.

17. The trocar assembly according to claim 15, wherein the band is a continuous ring.

18. The trocar assembly according to claim 15, wherein a distal end of the first portion of the trocar tip extends farther distally than a distal end of the second portion of the trocar tip after assembly of the trocar tip.

19. The trocar assembly according to claim 18, wherein a proximal end of the first portion of the trocar tip physically contacts the shaft when the trocar tip is mechanically engaged with the shaft.

20. The trocar assembly according to claim 15, wherein a distal end of the second portion of the trocar tip extends farther distally than a proximal end of the first portion of the trocar tip after assembly of the trocar tip.

* * * * *